(12) United States Patent
Mansmann

(10) Patent No.: US 6,530,956 B1
(45) Date of Patent: Mar. 11, 2003

(54) RESORBABLE SCAFFOLDS TO PROMOTE CARTILAGE REGENERATION

(76) Inventor: Kevin A. Mansmann, 250 W. Lancaster Ave., Suite 310, Paoli, PA (US) 19301

( * ) Notice: Subject to any disclaimer, the term of this patent is extended or adjusted under 35 U.S.C. 154(b) by 0 days.

(21) Appl. No.: 09/393,522

(22) Filed: Sep. 10, 1999

Related U.S. Application Data

(60) Provisional application No. 60/099,817, filed on Sep. 10, 1998.

(51) Int. Cl.$^7$ .............................. A61F 2/30; A61F 2/28
(52) U.S. Cl. ..................................................... 623/18.11
(58) Field of Search ........................... 623/18.11, 18.12, 623/19.11–19.14, 20.11–20.28, 16.11, 17.11–17.16

(56) References Cited

U.S. PATENT DOCUMENTS

| | | | |
|---|---|---|---|
| 3,867,728 A | * 2/1975 | Stubstad et al. | 3/1 |
| 5,702,449 A | * 12/1997 | McKay | 623/17 |
| 5,749,874 A | * 5/1998 | Schwartz | 606/75 |
| 5,769,899 A | * 6/1998 | Schwartz et al. | 623/18 |
| 6,102,948 A | * 8/2000 | Brosnahan, III | 623/17 |
| 6,143,032 A | * 11/2000 | Schafer et al. | 623/16 |
| 6,206,924 B1 | * 3/2001 | Timm | 623/16 |

\* cited by examiner

*Primary Examiner*—Corrine McDermott
*Assistant Examiner*—Hieu Phan

(74) *Attorney, Agent, or Firm*—Patrick D. Kelly

(57) ABSTRACT

A load-sharing resorbable scaffold is used to help transplanted chondrocytes or other cells generate new cartilage in a damaged joint such as a knee, hip, or shoulder. These scaffolds use two distinct matrix materials. One is a relatively stiff matrix material, designed to withstand and resist a compressive articulating load placed on the joint during the convalescent period, shortly after surgery. Due to the requirement for relatively high stiffness, this material must be denser and have less pore space than other matrices, so it will not be able to support highly rapid cell proliferation and cartilage secretion. The second material comprises a more open and porous matrix, designed to promote maximal rapid generation of new cartilage. In one preferred geometric arrangement, the stiffer matrix material is used to provide an outer rim and one or more internal runners, all of which can distribute a compressive load between them. The rim and runners create a cluster of internal cell-growing compartments, which are filled with the porous and open matrix material to encourage rapid cell reproduction and cartilage generation. These improved scaffolds can also have an articulating outer membrane with certain traits disclosed herein, bonded to and resting upon the upper edges of the runners and rim. The scaffold will support the membrane with a degree of stiffness and resiliency that allows the membrane to mimic a healthy cartilage surface. These scaffolds can be made of flexible materials, to allow them to be inserted into a damaged joint using arthroscopic methods and tools.

24 Claims, 4 Drawing Sheets

LEGEND:
- ○ SAPL
- ○ Lubricen
- ∞ Lubricen/SAPL complexes
- • Hyaluronic acid
- ⊙ Other macromolecules
- ⚌ Semi-permeable membranes

UNLOADED JOINT SPACE

INSTANTANEOUS LOADING

STATIC COMPRESSION

HYDROPLANING MOTION

LOADED FLUID FLOW THROUGH SELECTIVELY PERMEABLE MEMBRANES

RESORBABLE SCAFFOLDS TO PROMOTE CARTILAGE REGENERATION

RELATED APPLICATION

This application claims priority based on provisional patent application No. 60/099,817, filed on Sep. 10, 1998.

BACKGROUND OF THE INVENTION

This invention is in the field of surgery, and more particularly, surgery to repair cartilage in joints such as knees, shoulders, or hips. It relates to the use of "scaffold" devices that can be implanted in a joint with damaged cartilage, to help support certain types of transplanted cells (such as "chondrocyte" cells) which can generate new cartilage. As used herein, the phrase "damaged cartilage" is used broadly, and includes cartilage which has been damaged by mechanical trauma or other physical or inflicted injury or abrasion, or by a disease process, such as arthritis or osteoarthritis.

Background information on knee, hip, and shoulder joints, on cartilage tissue, and on "classical" techniques and devices that have been used for many years to repair damaged cartilage in knee joints are discussed in numerous medical texts, such as *Campbell's Operative Orthopedics*, a five-volume treatise. Additional information is periodically issued by the American Academy of Orthopedic Surgeons in a series of books called "Orthopedic Knowledge Updates"; volume 6 in that series was issued in 1999.

A number of recent articles and patents describe efforts to use transplanted chondrocyte cells, and various types of "precursor" and "stem" cells, to generate new cartilage. Such articles include Brittberg et al 1994, Chen et al 1997, Minas et al 1997, and Thornhill 1997 (complete citations are provided below).

Most of the patents in this field tend to concur that the best way to promote cartilage regeneration inside a joint involves the use of a "resorbable" matrix, made of a material such as collagen, the protein that normally holds together connective tissue and provides the three-dimensional matrix that tissue cells grow in. In any type of connective tissue, the existing collagen fibers are slowly and gradually digested, mainly by an enzyme called collagenase. This process of gradual digestion of the old collagen is matched by a gradual secretion of new collagen fibers by the cells in the tissue, resulting in a process of turnover and replacement that helps keep tissue flexible, healthy, and strong. Accordingly, collagen implants (usually made from cowhide, which offers an abundant source of the fibrous protein, treated with cross-linking and other chemical agents to control the rate of enzymatic degradation) were developed for other purposes beginning in the mid-1970's (e.g., U.S. Pat. No. 4,060,081, Yannas et al 1977).

Clearly, implantation of chondrocyte or similar cartilage-secreting cells in a damaged cartilage surface in a joint is a difficult and challenging task, which requires the cells to be anchored in position and then protected and sheltered from compressive and shear forces for a period of weeks or months, to give the transplanted cells a chance to generate firm and anchored cartilage without simply being squashed out of the joint. Accordingly, researchers began to realize by about the mid-1980's that resorbable collagen matrices could be used to help position, protect, and anchor such cells in cartilage repair operations, and if properly designed, the matrix would gradually disappear once it had accomplished its task, leaving behind regenerated cartilage.

Accordingly, a large number of US patents were issued which centered around this theme, and which proposed various ways to enhance and improve the ability of the "resorbable collagen matrix" approach to repairing damaged cartilage. For example, U.S. Pat. No. 4,846,835 (Grande 1989) discloses techniques for giving chondrocyte cells (preferably taken from the same patient who has suffered the joint damage, so that no risk of rejection will be present) a headstart, by growing them outside the body in an in vitro cell culture solution, seeded and embedded into a collagen matrix. After the cells have been growing inside the collagen matrix for a suitable number of days, under lab conditions, the entire matrix (including the cells) can be surgically implanted into the damaged joint.

U.S. Pat. No. 4,880,429 (Stone 1989), U.S. Pat. No. 5,007,934 (Stone et al 1991), and U.S. Pat. No. 5,306,311 (Stone et al 1994) also relate to porous matrices made of collagen or similar compounds, which can be shaped or sculpted in various desired shapes, then implanted or "seeded", under laboratory conditions, with cells that reproduce to form large numbers of chondrocyte cells (which generate cartilage) or meniscal fibrochondrocytes (which generate meniscal tissue);

U.S. Pat. No. 5,041,138 (Vacanti et al 1991) describes a similar type of cell growth, in a biodegradable matrix made of a synthetic polymer rather collagen.

U.S. Pat. No. 5,206,023 (Hunziker 1993) relates to a multi-step process for repairing damaged cartilage, involving (i) enzymatic treatment to remove proteoglycans from the defect area, followed by (ii) packing the cleaned area with a degradable matrix that encourages ingrowth of repair cells.

U.S. Pat. No. 5,518,680 (Cima et al 1996) discloses the use of various "solid free-form" manufacturing techniques which can be aided by "computer-assisted design" (CAD techniques, such as stereo-lithography, selective laser sintering, fusion deposition modeling, and three-dimensional printing, to rapidly manufacture colagen or other resorbable matrices in precise dimensions that are determined based on the dimensions of the defect in a particular patient. The '680 patent also discloses the incorporation of certain inorganic particles in such matrices, both to strengthen the highly porous matrices, and to provide a source of minerals for regenerating tissue.

U.S. Pat. Nos. 5,749,874 and 5,769,899 (both Schwartz et al 1998) disclose a two-component implant, where one component is a holding and anchoring device, made of a relatively hard yet biodegradable material such as polyglycolic acid, polylactic acid, or combinations therof. This anchoring device is designed to to hold a more porous and flexible matrix, made of a material such as collagen or hyaluronic acid, which will hold chondrocyte cells.

Various other patents focus on alternatives to collagen, in biodegradable matrices. Such patents include U.S. Pat. No. 5,294,446 (Schlameus et al 1994), which discloses that alginate (a naturally occurring polysaccharide) can be used to encapsulate of live cells. U.S. Pat. No. 5,041,138 (Vacanti et al 1991), U.S. Pat. No. 5,709,854 (Griffith-Cima et al, 1998) and U.S. Pat. No. 5,736,372 (Vacanti et al 1998) provide extensive information on various synthetic polymers (such as polyphosphazines, polyacrylates, polyanhydrides, and polyorthoesters, as well as "block copolymers" such as mixtures of polyethylene oxide and polypropylene glycol) which can be used to generate hydrogels which can used for cartilage replacement.

These listed patents also contain citations to numerous published articles that are directly relevant in this field. Alternately, an Internet search of the National Library of Medicine database, available for free at http://www.igm.nih.gov, combining "cartilage" as a subject or title word combined with "Langer" or "Vacanti" as an author name, will quickly provide a generous supply of information on the current state of the art in this field.

It should be noted that some of the polymers listed in the Vacanti et al patents cited above were chosen and developed to repair facial cartilage (mainly in the nose and ears) rather than for repairing load-bearing cartilage in joints. In general, cartilage in the nose and ears is softer and more flexible than "hyaline" or "articulating" cartilage which occurs in knees, hips, and other joints. Accordingly, although the '854 and '372 patents disclose and discuss a long list of potentially suitable biocompatible synthetic polymers, all of which can support chondrocyte growth for a prolonged period and then eventually disappear due to resorption, any synthetic polymer intended for use in a knee, hip, or other load-bearing joint will need to be selected accordingly, with careful attention to its load-bearing traits.

Two quantifiable traits which are important are called dynamic stiffness, and aggregate modulus. Dynamic stiffness is discussed in articles such as Vunjak-Novakovic et al 1999, and is usually expressed in this field of art in terms of megaPascals (mPa). The dynamic stiffness of natural hyaline cartilage is usually about 10 mPa. Aggregate modulus is discussed in articles such as Ma et al 1995, and is usually expressed in terms of kiloPascals (kPa). The aggregate modulus of natural hyaline cartilage is usually about 450 kPa.

A number of patents in this field of art focus on the use of specialized molecules which can stimulate certain processes that are useful during cartilage regeneration. An early patent in this field was U.S. Pat. No. 4,609,551 (Caplan et al 1986), which claimed that "soluble bone proteins" can induce certain types of cells to begin secreting cartilage. During the following decade, as various proteins were identified in greater detail, subsequent patents claimed that (i) certain "transforming factors" can be used to cause "precursor" chondrocytes or other "stem" cells to mature into chondrocyte cells that actively secrete collagen (e.g., U.S. Pat. No. 5,206,023, Hunziker 1993); (ii) certain "chemotactic" agents can be used to encourage "repair cells" to migrate into a cartilage defect being repaired (e.g., U.S. Pat. Nos. 5,206,023 and 5,270,300, both Hunziker 1993); and, (iii) certain "mitogens", also called "proliferation agents", can be used to cause chondrocyte cells to reproduce more rapidly (e.g., U.S. Pat. No. 5,206,023, Hunziker 1993). Each of those categories of hormones and "factors" is indeed useful for stimulating and accelerating the cellular processes disclosed herein, and the invention specifically anticipates that each one of those categories of biologically active agents can be used in conjunction with the resorbable matrices disclosed herein.

Still other patents disclose other proposed devices and methods for using transplanted chondrocyte or other cells to replace and repair damaged cartilage. For example, U.S. Pat. No. 5,759,190 (Vibe-Hansen et al 1998) suggests that a "hemostatic barrier" should be placed as a lining between a chondrocyte implant and the underlying cartilage, and that a protective "covering patch" such as a cell-free collegen membrane should also be placed on top of the chondrocyte implant. U.S. Pat. No. 5,786,217 (Tubo et al 1998) discloses a method of growing a complete intact piece of cartilage outside the body, using in vitro methods and a pre-shaped growing well, and then surgically implanting the piece of cartilage into the defect, using sutures and/or adhesives to anchor it. U.S. Pat. No. 5,842,477 (Naughton et al, 1998) discloses the use of certain types of periosteal and/or perichondrial tissue in conjunction with chondrocyte implants, to promote the migration of chondrocyte, progenitor, or stromal cells into the area being repaired.

Despite all of the foregoing, the methods and devices disclosed in the articles and patents cited above suffer from various limitations. Perhaps the most important limitation arises from the fact that under the current state of the art, chondrocyte cell transplants can only be used to repair cartilage defects that are about 1 square centimeter, or smaller, in size. Diligent efforts to work with larger areas have been tried, but the success rates in such efforts decrease when the size of the cartilage defect increases, and by the time a defect that needs to be repaired covers about 2 square centimeters or more, the success rate is very low. Therefore, repair of a large defect in a cartilage surface of a knee normally requires a "total knee replacement." Accordingly, although chondrocyte transplants are useful for treating many types of sports injuries and other types of mechanical trauma or injury (such as automobile or bicycling accidents, falls, etc.), they are severely limited, and in most cases totally useless, for treating elderly patients, patients suffering from osteoarthritis, and various other types of patients with defects larger than about 1 to about 1.5 square centimeters.

In addition to that size limitation, collagen or other porous proteinaceous matrices disclosed in the patents by Stone, Hunziker, or Grande are not tough and durable, so it is difficult or impossible to anchor them to a bone surface that is subject to loading conditions.

It also should be recognized that repair methods involving transplanted chondrocyte cells under the prior art require long recovery times, compared to other approaches such as a "total knee replacement" using a mechanical joint. Typically, a patient receiving a chondrocyte cell transplant in a knee joint is prohibited from putting any weight on the knee for at least 6 weeks, and many patients are told to not put any weight on the knee for even longer periods, such as 12 weeks. Even after a patient can begin using the knee again, full recovery from chondrocyte cell transplant surgery typically requires numerous months. This type of slow and prolonged recovery period greatly increases the total costs of treatment and recovery (including, in many cases, lost work and lost wages). By contrast, a patient who has a "total knee replacement" (TKR, which involves sawing off and removing a damaged knee joint and replacing the joint with a mechanical device attached to the tibia and femur bones by steel pins) can usually begin to put weight back on the knee within a day or two after the surgery.

The very long recovery period required by chondrocyte cell transplants under the prior art also tends to limit candidate patients to relatively young people who were injured in a sporting event, auto accident, etc. Elderly patients, who are not as active and who will not have to live with a serious knee problem for another 40 years or more, are usually advised to get "total knee replacement" surgery instead.

Accordingly, one object of this invention is to disclose improved methods and devices for using transplanted cells to help repair damaged cartilage in a joint, using scaffold devices to enlarge the area and volume that can be treated by the transplanted cells.

Another object of this invention is to disclose a resorbable scaffold device made of two different materials. One is a relatively stiff matrix material, to provide load-bearing support. The other matrix material is designed for maximal rapid generation of new cartilage, and can be substantially softer and more highly porous.

Another object of this invention is to disclose a method of enlarging the size of an area of damaged cartilage that can receive transplanted chondrocyte or other cells, by means of a resorbable scaffold that effectively subdivides the large area into a cluster of smaller areas, each of which is surrounded and protected by walls and "runners" made of the relatively stiff matrix material.

Another object of this invention is to disclose a method of combining two different and distinct technologies (chondrocyte cell transplants, and flexible scaffold devices that can be inserted into a joint using arthroscopic tools and minimally-invasive incisions), to provide a hybrid form of treatment that offers improved methods of arthroscopic repair of damaged cartilage in joints such as knees.

These and other objects of the invention will become more apparent through the following summary, drawings, and description of the preferred embodiments.

SUMMARY OF THE INVENTION

A load-sharing resorbable scaffold is used to help transplanted chondrocytes or other cells generate new cartilage in a damaged joint such as a knee, hip, or shoulder. These improved scaffolds use two distinct types of porous matrix materials. One is a relatively stiff matrix material, which is designed to withstand and resist a compressive articulating load that is placed on the joint during the convalescent period shortly after surgery. Due to the mechanical requirement for a relatively high stiffness, this matrix material must be denser and have less pore space than other available matrices. Accordingly, it will not be able to support as much cell proliferation and cartilage secretion as other matrices which have higher levels of porosity. The second type of material comprises a more open and highly porous matrix material which is designed to promote maximal rapid generation of new cartilage. In one preferred geometric arrangement, the stiffer matrix material is used to provide an outer rim and one or more internal runners, all of which can distribute a compressive load between them. The rim and runners create a cluster of internal cell-growing compartments, which are filled with the more porous and open matrix material to encourage rapid cell reproduction and cartilage generation.

These improved scaffolds can also have an articulating outer membrane with certain characteristics disclosed herein, bonded to and resting upon the upper edges of the internal runners and outer rim. The scaffold will support the outer membrane with a degree of stiffness and resiliency that allows the membrane to mimic a healthy cartilage surface.

As a further option, these scaffolds can be made of flexible materials. This will allow them to be inserted into a damaged segment of cartilage using arthroscopic methods and tools, to minimize surgical damage to tissue and blood vessels in the vicinity of the joint.

DESCRIPTION OF THE PREFERRED EMBODIMENTS

Figures 1, 1A:
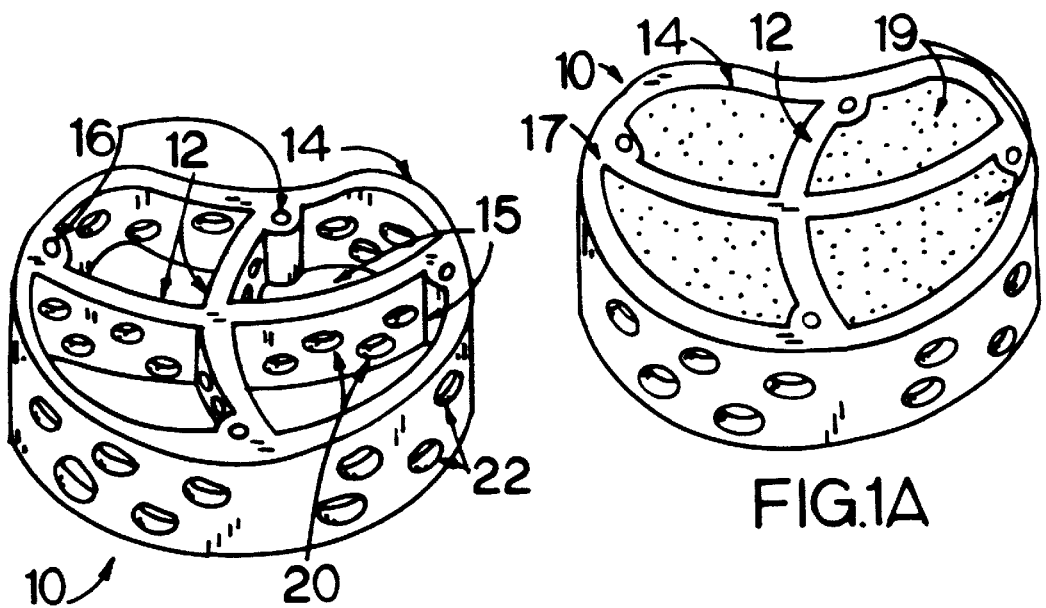
FIG. 1 depicts a scaffold 10 made of a relatively stiff matrix material, to help repair a damaged segment of cartilage on a tibial plateau. The internal runners and outer rim divide the scaffold into four cell-growth compartments, each of which covers an area less than 1 square centimeter.
FIG. 1A depicts the same scaffold 10 shown in FIG. 1, with the four internal compartments filled with four segments of a matrix material which has greater porosity, for maximal rates of cell growth and cartilage secretion within those compartments.

Referring to the drawings, callout number 10 in FIG. 1 refers to a "compartment scaffold", with internal runners 12 and an outer rim 14. The rim 14 and runners 12 interact to divide scaffold 10 into 4 internal compartments 15, referred to herein as cell-growth compartments. Scaffold 10 is designed to be used in an operation involving transplanted chondrocyte cells, to help repair a defect in a segment of cartilage on a tibial plateau. It is made of a first matrix material which is relatively stiff, and which is designed to withstand and resist a compressive articulating load placed on the joint after the scaffold has been surgically implanted, before substantial resorption begins to occur.

Because of its relative stiffness, scaffold 10 is referred to occasionally as a "load-sharing" scaffold. It is a porous matrix, made of collagen or a suitable biocompatible and porous polymer, and it gradually resorbs when in contact with body fluids. Because of its porous nature and material of construction, it allows growth and cartilage secretion by transplanted cartilage-secreting cells embedded therein; however, because of the load-sharing demands placed on this material, it generally is required to be (i) more dense than is optimal for rapid cell growth and cartilage secretion; and/or (ii) made of material which is selected largely for strength and which is not optimal for rapid cell growth and cartilage secretion.

The load-sharing scaffolds herein are especially useful for, but are not limited to, the repair of large defects in cartilage. As used herein, a "large" defect generally refers to a cartilage defect that covers or adversely affects a surface area larger than about 1 square centimeter (cm). As noted above, success rates using transplanted chondrocyte cells to repair cartilage defects drop off sharply when the defect is larger than about 1 square cm. Accordingly, one of the goals and purposes of this invention is to enable the repair of large defects, using transplanted chondrocyte cells, by allowing a large defect to be subdivided into smaller compartments, each of which can then be treated simultaneously in a manner suitable for treating a small defect.

Terms such as "damaged cartilage" and "cartilage defect" are used interchangeably herein, and are used in the broad sense. Either term refers to a segment of cartilage that suffers from any type of damage or defect that appears to be amenable to repair or improvement using transplanted chondrocyte cells, regardless of whether the problem was caused by mechanical trauma, a disease such as arthritis or osteoporosis, etc. Terms such as "repair" are also used broadly, and refer to a surgical or arthroscopic procedure which improves the condition of a segment of damaged cartilage, even if such improvement does not rise to the level of a total and perfect cure.

It also should be noted that this invention is not limited to treating defects that are larger than 1 square cm. This invention can also be evaluated and tested for treating smaller cartilage defects, such as defects in the size range of about 0.5 to about 1 square cm, to determine whether the success rates for treating such defects can be improved through the use of a compartmented scaffold as described herein.

Reference herein to "articulating surface" refers to the well-known fact that, in a healthy joint, two cartilage-covered surfaces on two different bones will rub, slide, roll, or otherwise move while in contact with each other, as the joint is flexed or extended. This type of mobile interaction between two such surfaces is referred to as articulation, and the two cartilage-covered surfaces that contact and press against each other during such motion are said to "articulate". Accordingly, a scaffold as disclosed herein has an anchoring side (which will be pressed against the bone to which the scaffold is anchored), and an articulating side or surface (which will be exposed, after the scaffold has been anchored to a bone). The anchoring side will be open, and will not be covered by a membrane, so that it will be in fluid communication with the bone surface to which it is anchored.

The articulating side of a scaffold can be covered by an articulating (outer) membrane, if necessary or appropriate, to provide the implanted chondrocyte cells with additional protection. Articulating membranes are discussed below.

The periphery of scaffold 10 is created by an outer or peripheral rim 14, which establishes the outer boundary (and the size) of the scaffold. In one preferred embodiment, outer rim 14 is made of essentially the same material as the internal runners 12, so that it contributes the same type of load-sharing support as the runners 12. In an alternate preferred embodiment, outer rim 14 is made of a material that resorbs more slowly than the internal runners 12, to provide the transplanted chondrocyte cells additional time to generate a fully solidified plug of cartilage inside the outer rim 14 before that outer rim dissolves and disappears. Animal and clinical tests can help determine which embodiment is preferred, and can indicate whether one type of scaffold is better suited for certain types of repairs while the other type is better suited for other types of repairs.

In scaffold 10, as shown in FIG. 1, the internal runners 12 have a plurality of orifices or "runner vents" 20, which pass through the walls of the runners 12. In addition, outer rim 14 also has a plurality of "rim vents" 22. As discussed below, runner vents 20 are designed to allow transplanted chondrocyte cells to generate "bridges" of cartilage between the four compartments of the scaffold 10. These bridges can help the four separate "plugs" of cartilage that will be formed in the compartments to gradually grow together into a single substantially larger plug that fills the entire outer rim 14, as the runners 12 are gradually dissolved and resorbed.

Similarly, the rim vents 22 are designed to allow transplanted chondrocyte cells to generate "bridges" of cartilage between the scaffold compartments, and the surrounding "walls" of native cartilage. As discussed below, in order to prepare a cartilage covered area to receive this type of implant, the surgeon will remove a certain amount of cartilage from the damaged area, in a manner that allows scaffold 10 to be securely placed within the cleared area, so that the "anchoring surface" of scaffold 10 will be pressed against an exposed bone surface from which all native cartilage has been removed. To maximize the success rates of such chondrocyte transplant operations, steps should be taken (such as providing vents in the outer rim 14 of scaffold 10) to ensure that the regenerated cartilage merges smoothly with the surrounding cartilage, into a single repaired layer of cartilage, rather than forming a separate plug of cartilage that does not eventually join and merge smoothly with the surrounding cartilage.

As noted above, the rim 14 and runners 12 of scaffold 10 establish four internal compartments 15, which are intended to be filled with a material that promotes rapid cell growth, and rapid cartilage secretion. Such materials can comprise a second and different type of matrix material, such as the material indicated by matrix segments 19, in FIG. 1A. Such matrix material which is designed to optimize and accelerate cell growth and cartilage secretion is likely to be substantially more porous than a load-sharing matrix material that must be strong enough the effective resist a compresive load.

However, it should be noted that the two distinct types of matrix material (i.e., the stiffer material in load-sharing scaffold 10, and the cell-growth material in matrix segments 19) might, if desired, be made from a single set of shared feedstock (such as collagen fibers or polymeric material) which has been treated differently in a manner that generates higher strength in the load-sharing portions and higher porosity in the cell-growing portions. As one example, a first aliquot from a batch of collagen fibers can be poured into a mold to form scaffold 10, and then subjected to a first cross-linking reaction. Subsequently, a second aliquot from the same batch of collagen fibers might be poured into the internal compartments of scaffold 10, and the entire set of material can be subjected to a second cross-linking reaction.

Alternately, in some patients it may be preferable to surgically implant and anchor scaffold 10 in a cartilage defect, using arthroscopic procedures, and then insert pre-formed matrix segments 19 into the internal compartments formed by scaffold 10.

In either situation, both the scaffold 10 and the cell-growth matrices 19 can be loaded (seeded) with cartilage-secreting cells, or their precursors (generally referred to as "stem" cells) either prior to the surgical operation, or as part of the surgical implantation procedure.

As a third alternative, scaffold 10 can be surgically implanted in a cartilage defect, and then filled with a slurry or paste which contains cells and a suitable additional material, such as alginate and/or a preparation containing the building blocks of cartilage, or any other fluidized or powdered substance which will be gradually converted by the transplanted cells into new cartilage.

In any of these cases, the resorbable scaffold can be regarded as an implantable device which has (i) an outer (articulating) surface 17, which will be exposed after the implantation; and, (ii) an opposed anchoring surface, which will be pressed against a bone or cartilage surface after the implantation. The scaffold will essentially comprise two or more wall components which extend from the articulating surface to the anchoring surface. These wall components will subdivide the cartilage defect surface area into smaller areas, and will create a plurality of protected enclosed compartments, each of which will promote chondrocyte cell maturation and development of hyaline cartilage within that protected enclosed compartment.

It is anticipated that a surgeon who is ready to commence an implanting operation can have an assortment of scaffolds, with a variety of different sizes and shapes, each of which is contained in a sealed sterile package. Once the surgeon has entered the knee (or other joint) with arthroscopic tools, and has inspected the cartilage defect to see exactly how large it is, the surgeon can select a scaffold from the assortment that is available, and choose a scaffold having the best size and shape for treating that particular defect.

The surgeon will then prepare the area by removing a relatively small amount of existing cartilage which surrounds the defect, to prepare an exposed subchondral bone surface that can support the growth of new cartilage on its surface. This preparative step will typically use a scalpel and curette. If desired, the surgeon can also use other tools, such as a grinding burr to ensure complete removal of the cartilage from the prep area, a drill bit or piercing device to puncture the bone surface and ensure a blood supply to the implanted cartilage cells, etc.

Once the bone surface has been properly prepared by removing a small quantity of existing cartilage from around the defect, the flexible scaffold can be rolled or folded up, inserted into the knee or other joint (preferably through a minimally invasive incision), unfolded into its proper final shape, and positioned in the prepared area from which the damaged cartilage was removed, so that the bottom edges of the outer rim and internal runners of the scaffold press solidly against the prepared bone surface.

When the scaffold has been properly positioned inside the defect area, it can be anchored to the bone using any suitable type of pin, staple, or other anchoring device. A variety of such devices (including pins and staples made of resorbable material) are commercially available, and are used today for purposes such as anchoring a "flap" of cartilage to its bed so it can heal properly.

Several anchoring sleeves 16 are shown positioned around the outer rim 14 of scaffold 10. If anchoring sleeves are sued which extend to the full height of the scaffold, as shown, the upper (articulating) surface of each anchor sleeve preferably should be recessed, in a small circular area surrounding the hole, to accommodate a flattened circular anchor head that will fit snugly in the recessed space. Alternately or additionally, staples can be used to secure one or more "lesser" runners that do not rise up to the full height of the scaffold, as discussed below.

After scaffold 10 has been properly positioned on a prepared bone surface surrounded by native cartilage, the compartments created by runners 12 and rim 14 will be filled with transplanted chondrocyte cells, usually contained in a highly viscous paste-type carrier, or in a cohesive fibrous matrix made of collagen or a similar material. The proper method of loading the cells into the compartments will depend on whether the scaffold has an articulating membrane, as discussed below.

Articulating Membranes

As noted above, the articulating surface of a scaffold can be covered by an articulating (outer) membrane, whenever necessary or appropriate. Such a membrane can provide implanted chondrocyte cells with additional protection from the various loads and stresses that are imposed on the scaffold. In addition, if an articulating membrane is designed and manufactured properly with a suitable degree of flexibility, it can help ensure that weight-bearing loads are distributed and imposed evenly on all of the runner compartments, to help ensure that cartilage which is regenerated in the scaffold compartments has a more uniform and consistent density and firmness.

Since it would hide the runners, an articulating membrane is not shown in the illustration of scaffold 10, in FIG. 1. Instead, FIG. 2, which provides a cross-sectional view of patellar scaffold assembly 30 anchored to patellar bone 31, and femoral scaffold assembly 50 anchored to femur 51, shows articulating membranes 32 and 52.

The ability of an articulating membrane to improve the likelihood of success of a specific repair operation in a specific patient will generally increase when: (i) a very large defect must be repaired; (ii) a cartilage segment having one or more relatively sharp or narrow curvatures in its surface must be repaired; or, (iii) two compartmented scaffolds are used simultaneously to repair two surfaces that press and articulate against each other, such as on a femoral condyle and a tibial plateau which are on the same side (medial or lateral) of a knee joint.

However, in other situations, an articulating membrane covering the scaffold compartments may not be essential, especially if the packing material used to load the chondrocyte cells into each compartment in the scaffold has sufficient cohesion and strength. Cohesive but resorbable packing materials can be provided by devices such as three-dimensional collagenous matrices or resorbable synthetic polymers, as discussed below.

At least three different types of articulating membranes can be provided; the preferred type which will give the best results in a specific repair operation on a specific patient can be determined by the surgeon treating that patient. The three categories of articulating membranes are referred to herein as permanent membranes, transforming membranes, and resorbing membranes.

A resorbing membrane is designed and intended to be gradually digested and dissolved, mainly by extracellular enzymes, so that it will disappear and be replaced by a natural biological surface. Because the remnants of a partially-digested membrane may act as debris that may clutter up or even damage the articulating interface during the intermediate stages of degradation, this approach generally is not regarded as the most initially promising approach for this type of joint repair, especially in knee joints. However, resorbing membranes may be useful in other joints, and they can be tested and evaluated in any type of joint, including knee joints, using lab animals. If good results are obtained in animal tests, this approach may be quite valuable, especially if a resorbable membrane can be developed which, without generating particulate debris, will instead act as though it has become permanently cemented to the surface it contacts, so that any digestion byproducts will diffuse in a direction that carries it into the cellular matrix and toward the bone surface that supports that membrane, without releasing debris into the synovial fluid that lubricates an articulating surface between two cartilage layers.

A permanent membrane is designed and intended to remain in the joint for the entire remaining life of the patient, in an essentially unmodified form. As such, it must be completely non-resorbable and highly resistant to biological degradation. Various types of non-resorbing biocompatible synthetic polymers can be used for such purposes.

In one preferred embodiment, a permanent synthetic membrane can be cemented to the upper surface of a set of resorbable supporting runners, so that the supporting runners will be gradually resorbed and replaced by newly-generated cartilage, while the permanent membrane remains intact as the articulating surface layer which covers and protects the supporting structures. In an alternate preferred embodiment, a permanent synthetic membrane can be permanently supported by a set of non-resorbable runners, presumably made of the same type of non-rigid synthetic polymer, so that the articulating membrane and runners all remain in essentially unchanged condition inside the joint, while the transplanted chondrocyte cells generate additional cartilage that will provide additional support and stability for the permanent membrane.

A transforming membrane is also designed to remain inside the joint for the life of the patient; however, unlike a synthetic permanent membrane, it will be acted upon by cells and enzymes in ways that convert it into a modified final form. This type of membrane can take advantage of certain healing and regenerating activities that occur after a bone has been broken, when the damaged tissue must repair itself and regenerate a fully healed and functional bone surface with a "periosteal" membrane covering the surface of the bone.

To create a transforming membrane, a segment of periosteal or perichondrial membrane can be harvested from elsewhere in the patient's body (or from another source, as discussed below). Under laboratory conditions, this membrane segment (which will already contain some chondrocytes and stem cells) can be saturated, coated, or otherwise loaded with a liquid that contains both (i) cultured chondrocytes, or certain types of "stem cells" that will transform into chondrocytes if contacted by certain hormones that act as "transforming factors"; and (ii) various naturally-occurring compounds such as collagen, "procollagen" building blocks, glycosaminoglycans, and other components that are converted and assembled by cells into load-bearing structural components such as cartilage. Under the proper conditions, after implantation into a load-bearing joint, the chondrocytes or stem cells that are on or in the harvested membrane segment will begin to organize the available biomaterials into a load-bearing surface, effectively using the implanted segment of membrane in a manner analogous to a canvas that an artist uses to create a painting.

Under the current state of the art, which is limited to repairing only relatively small defects, most chondrocyte transplant procedures require elaborate steps to harvest a small piece of periosteal tissue from somewhere in the patient's body, so it can be used for the procedure. However, methods have been developed in other fields of surgery (most notably involving replacements for damaged heart valves) for chemically treating tissues segments that have been harvested from human cadavers, or even from completely different species (mainly pigs). This type of chemical treatment for "allograft" or "xenograft" tissue can likely be adapted to develop effective ways of treating large segments of periosteal or perichondrial membrane harvested from cadavers or animals, in ways that will render such treated membranes suitable for transplantation into a knee or other joint, to create a "transforming membrane" as described herein. U.S. Pat. No. 4,627,853 (Campbell et al 1986) and U.S. Pat. No. 5,782,915 (Stone 1998) describe various methods that can be used to treat bone or cartilage tissue from cadavers or non-human species, to render the treated tissue non-immunogenic and suitable for transplanting into humans. It should also be noted that substantial efforts have been made to genetically engineer certain types of animals, so that tissues harvested from the animals will have reduced antigenicity and will be less likely to provoke an immune response if implanted into a human. Such efforts are discussed in articles such as Rosengard et al 1992.

The proper selection of a permanent (synthetic), transforming, or resorbing articulating membrane for repairing a specific joint in a patient (and the need for an articulating membrane to cover a compartmented scaffold) will depend on factors that will need to be evaluated, for each patient, by the surgeon who is treating that patient. The factors that will be relevant in reaching such decisions include: (i) which joint is involved, and what types of stresses it is subjected to in that particular patient; (ii) the etiologic factor which caused the cartilage damage; (iii) the condition of the joint, and of the damaged cartilage segment(s) in that joint; and, (iv) the size, weight, age, lifestyle, physical activity level, and overall medical condition of the patient.

If an articulating membrane is used with a compartmented scaffold as disclosed herein, the membrane must have a combination of traits that will allow it to function as an articulating surface in a functioning joint. The primary desirable traits include: (i) a very smooth surface, to promote sliding and articulation with very little friction, resistance, "grabbing," or abrasion; (ii) a hydrophilic nature, to ensure constant wetness and lubrication of the articulating surfaces by the naturally occurring synovial fluid in a joint; (iii) physiological acceptability and biocompatability, which requires that it must not provoke blood clots, an immune rejection response, or other adverse events known to those who specialize in biocompatible implants; and (iv) permeability to synovial fluid nutrients.

Runner-protected Compartments and Packing Materials

Figure 2:
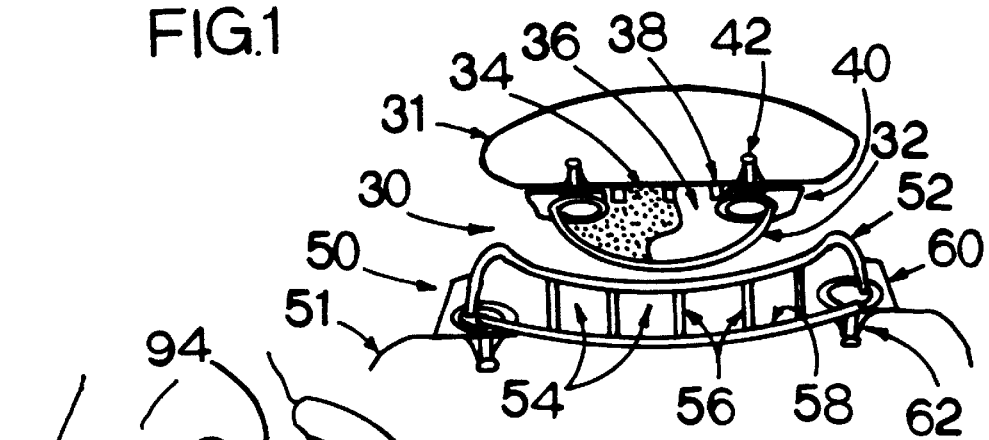
FIG. 2 is a cross-sectional view showing a femoral scaffold and a patellar scaffold which "articulate" against each other. The femoral scaffold depicts a row of compartments, separated from each other by runners and covered by an articulating membrane, such as a periosteal membrane segment.

FIG. 2 is a cross-sectional view of a femoral-patellar compartment (i.e., the interface between the thighbone and the kneecap). The lower part of FIG. 2 depicts a femoral scaffold assembly 50, with a row of compartments 54 that are separated from each other by a series of parallel runners 56. The runners 56 are bonded to and support an articulating membrane 52.

Callout number 58 in FIG. 2 does not indicate an anchoring membrane; there is no such membrane, since scaffold compartments 54 should be in fluid communication with the exposed bone surface. Instead, item 58 is a small "reinforcing runner" that runs perpendicular to the load-sharing runners 56. The reinforcing runner 58 connects the bases of load-sharing runners 56 to each other, in order to provide them with additional reinforcement and support, and to help ensure that the load-sharing runners 56 return to an even spacing, a proper distance apart from each other, after the flexible scaffold is twisted, manipulated, and distorted while being inserted and implanted into the knee. This same type of small runner is shown, from a different perspective, as reinforcing runner 38 in patellar scaffold assembly 30, in the upper half of FIG. 2.

Femoral scaffold assembly 50 is anchored to the anterior surface of femur bone 51 with the assistance of a positioning ring 60, which has an open center (with no membrane), and which is anchored to femur 51 by means of a plurality of femoral anchors 62. The positioning ring 60 and anchors 62 are described in more detail in the utility patent application that is included herewith as Appendix A.

The upper half of FIG. 2 depicts a patellar (kneecap) scaffold assembly 30, with load-sharing runner 36 shown in a partial cutaway view. This cutaway view also depicts a slurry or matrix 34, which is loaded with transplanted chondrocyte cells.

The load-sharing patellar runner 36 is oriented perpendicular to the load-sharing femoral runners 56, as discussed below, to reduce any catching, grabbing, or other undesired interactions between the two sets of runners (patellar and femoral) as they press and slide against each other, during articulation.

As with the femoral scaffold, the patellar scaffold assembly 30 is anchored to the posterior surface of patella bone 31, with the assistance of a positioning ring 40 and a plurality of patellar anchors 42.

In femoral scaffold assembly 50, each compartment 54 (separated by the load-sharing runners 56) is a volumetric space or gap where cultured chondrocyte cells (prepared as described below) are implanted. After the operation, the chondrocyte cells can grow, reproduce, and secrete new cartilage within each and all of the various compartments 54. Accordingly, each compartment 54 functions as a protected environment, comparable to a nursery as discussed below. The load-sharing runners 56, acting in conjunction with the articulating membrane 52, will shelter and protect the transplanted chondrocyte cells from the excessive weight-bearing loads and other physical stresses that are imposed on articulating surfaces in knee joints.

However, it must also be recognized that the load-sharing runners 56 are not designed or intended to completely isolate the transplanted chondrocyte cells; the runners must not shield the cells from all weight-bearing loads, and must not generate a completely stress-free environment. Instead, the transplanted chondrocyte cell material must be subjected to moderate loads, to cause the cells to generate cartilage. In general, chondrocyte cells that are subjected to loading conditions while having an adequate vascular blood supply will often generate bone; by contrast, chondrocyte cells that are subjected to loading stresses under "avascular" conditions (i.e., without a steady supply of blood) will often generate cartilage. Accordingly, scaffold runners as disclosed herein must be designed and used in ways that will effectively help generate cartilage-producing (i.e., avascular and moderately loaded) conditions within the scaffold.

To help express the concept of this invention, the protected runner-protected compartments provided by a scaffold as disclosed herein are referred to collectively as a "nursery" for chondrocyte cells. This emphasizes the functional similarities between: (i) a "nursery in a knee", which is designed to help protect chondrocyte cells that have been transplanted into a high-stress location in a damaged joint that needs repair; (ii) a hospital nursery, where newborn babies are carefully tended and taken care of until they've survived the perilous neonatal transition; and (iii) a plant nursery, where sprouts, saplings, and other infant plants are carefully watered, fertilized, and protected from weeds and insects until they've matured and grown strong enough to stand on their own and defend themselves without as much high-maintenance care from others. In each of these contexts, a nursery is not intended as a permanent residence; instead, it merely offers temporary protection during a difficult and dangerous transition.

Accordingly, the goal, purpose, and function of scaffolds with runners and cell-growing compartments as disclosed herein is to protect small pockets of transplanted biological materials (including chondrocyte cells and possibly certain types of pluripotential or mesenchymal "stem cells," mixed with various nutrients, cell transforming or activating factors, and molecules the cells can use to synthesize or organize collagen or glycosaminoglycans), until the cells organize and create a biological load-bearing surface.

In one preferred embodiment, the load-bearing runners that help support a scaffold will be gradually digested and resorbed by enzymatic activity. As that process continues (aided by various types of physical therapy, such as using "continuous passive motion" (CPM) machines to flex and extend a repaired knee for substantial periods of time each day during the initial recovery period), the cells that have been transplanted into a runner-protected compartment will commence what is, in essence, a defensive physiologic response to gradually increasing levels of stress. The cells will organize and secrete more cartilage, since the new cartilage can help protect the cells by accepting and bearing a gradually increasing portion of the load that is being imposed on that articulating surface. This type of gradually changing biomechanical environment, where a weight-bearing load is gradually shifted away from a slowly dissolving artificial implant and transferred to a slowly growing biological component, can help promote proper in vivo development of a viable and durable load-bearing cartilage surface, inside the joint that is being repaired.

Any of several types of previously known materials offer good candidates as preferred materials that can be used to load chondrocyte or stem cells into the runner-protected compartments of a scaffold as disclosed herein. Types of cell-packing materials that appear to merit evaluation for possible use as disclosed herein include: (i) collagen-containing matrices, including matrices that also contain other ingredients and which have been chemically treated to control the rate of degradation and resorption of the matrix, as described in various publications and various patents such as U.S. Pat. No. 4,846,835 (Grande 1989), U.S. Pat. No. 5,206,023 (Hunziker 1993); U.S. Pat. Nos. 4,060,081 and 4,280,954 (Yannas and Burke 1977 and 1981) and U.S. Pat. Nos. 4,880,429 and 5,306,311 (Stone 1989 and 1994); (iii) matrices made of synthetic polymers that are biodegradable, as disclosed in U.S. Pat. No. 5,041,138 (Vacanti et al 1991); and, (iii) demineralized bone material, as described in various patents such as U.S. Pat. No. 4,627,853 (Campbell et al 1986). The choice of packing material is not essential to this invention, and different packing materials are likely to be preferred for treating different types and sizes of cartilage defects. In general, the compartmented scaffolds disclosed herein can protect and promote chondrocyte cell growth and cartilage synthesis in any type of packing material that is chosen by a surgeon to treat a specific patient in a specific operation.

Design and Arrangement of Runners

In a compartmented scaffold as disclosed herein, there will be at least two or more scaffold compartments, separated from each other by runners. The number of compartments in a particular scaffold used to repair a particular defect will depend mainly on (i) the size of the defect, and (ii) the size and shape of the compartments that are preferred for use with a particular type of cell-packing material, which will be selected by a surgeon for a specific operation.

As noted above, prior reports by various surgeons have indicated that cartilage defects up to about 1 square centimeter in surface area can be repaired with fairly good success rates; however, success rates drop sharply when attempts are made to repair defects larger than about 1 square centimeter. In view of those published reports, this invention can be regarded as providing a method and device for effectively subdividing a large defect in a damaged segment of cartilage into two or more smaller zones, by using runners, wherein each zone (compartment) will be less than 1 square centimeter in size. Each scaffold compartment can have chondrocyte cells loaded into it, and the chondrocyte cells can then synthesize cartilage within that relatively small compartment, in a manner that can achieve the high success rates that have previously been achievable only when small defects were repaired.

Accordingly, in one preferred embodiment, a scaffold as disclosed herein can be subdivided into a relatively small number of runner-protected compartments, wherein each compartment covers a total surface area in a range of about 0.5 to about 1 square cm. In this preferred embodiment, a surgeon who is about to commence an operation can have an assortment of different compartmented scaffolds, in a variety of different sizes and shapes. Each such scaffold will be contained in its own sealed and sterile package, which will be opened only when that scaffold has been selected for use during a surgical or arthroscopic procedure on a specific patient.

A suitable number of days prior to the surgery, the surgeon can remove one or more small plugs containing viable chondrocyte or stem cells from a healthy bone or cartilage area, using tools and methods such as described in U.S. Pat. No. 5,782,835 (Hart et al 1998). The chondrocyte or stem cells are isolated, using various chemical treatments, and then cultured under carefully controlled conditions that involve specialized nutrients, transforming factors, mitogenic factors, etc. These treatment factors used during the culturing period will cause the cells to divide and reproduce in large numbers, in in vitro culture, thereby generating a greater supply of chondrocyte cells. Methods and active biological agents for use in this type of cell culturing are described in various published reports, and in various patents such as U.S. Pat. No. 5,041,138 (Vacanti et al 1991) and U.S. Pat. No. 5,206,023 (Hunziker 1993).

When the cell culturing procedure has reached a desired stage, the surgical operation can begin. After arthroscopically examining the defect in the patient's cartilage, the surgeon will select a scaffold which has an appropriate size and shape for treating that defect. The surgeon will then prepare the bone surface to receive the scaffold, usually by using one or more scalpels and curettes to remove all of the cartilage from a subchondral bone surface in a certain area. Once the bone surface has been prepared, the surgeon will open a sealed package containing a flexible scaffold that has the desired size and shape, and will insert the flexible scaffold into the knee, preferably through a minimally-invasive incision (although open surgical methods can be used when appropriate, especially if a joint suffers from multiple types or sites of damage).

If a scaffold does not have an articulating membrane, and if cultured chondrocyte cells can be loaded into the runner compartments from the top side, then the scaffold should be fully anchored to the subchondral bone surface before the cells are loaded into it.

Alternately, if a scaffold contains an membrane which covers the articulating surface of the scaffold and prevents loading of cells into a scaffold that has already been fully anchored to a bone surface, the scaffold can positioned in an approximate manner over the defect, without being fully anchored. For example, one edge can be glued to a positioning ring, as shown by positioning rings 40 and 60 in FIG. 2 or one or more anchor pins or staples can be emplaced at or near the distal end of the scaffold's outer perimeter. This will establish the final position of the scaffold and give it a temporary "flap" structure, with a fixed distal end and an open proximal end. The surgeon can then emplace the cultured chondrocyte cells in the scaffold compartments, on the underside of the scaffold, before completely anchoring the scaffold to the prepared bone surface.

The cell placement step can be done in any of several ways. For example, a surgeon can use an injection tube or other device to inject cells that are contained in a paste, slurry, or other viscous carrier fluid, into a scaffold compartment. Alternately, a surgeon can insert a properly sized segment of a cohesive matrix (made of a material such as collagen or a biodegradable synthetic polymer) which has been saturated with a liquid solution containing the cells, into a scaffold compartment. Such matrix segments can be pre-cut to specific desired sizes which will correspond to the runner-protected compartment sizing in the scaffold; additional segments having any desired size or shape can be custom-cut by the surgeon, if desired, for purposes such as filling in small peripheral gaps between an outermost scaffold runner and the cartilage face of the perimeter of the prepared surface. After the cells have been emplaced properly in the runner-protected compartments, the surgeon finishes securing and attaching the scaffold.

Figure 3:
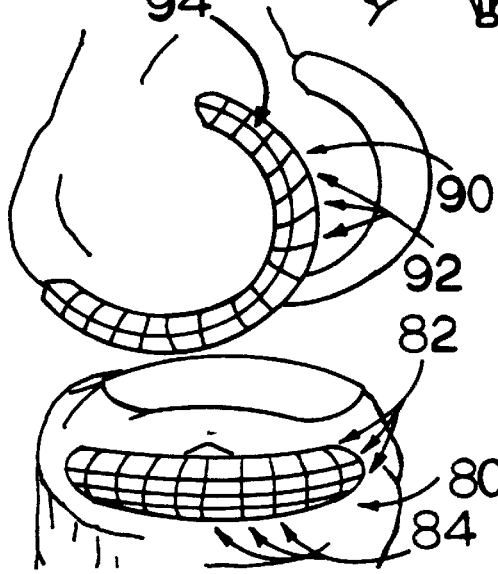
FIG. 3 depicts a set of longitudinal load-sharing runners in a tibial scaffold, and a set of transverse load-sharing runners in a femoral scaffold that articulates against the tibial scaffold. Orienting the load-sharing runners in different directions will minimize any catching, friction, or other undesired interactions between the two scaffolds, or between the repaired cartilage surfaces that are generated with the assistance of the scaffolds.

If two articulating scaffolds will press and rub against each other, the load-sharing (prominent) runners in the two scaffolds preferably should be oriented in different directions. For example, FIG. 3 shows a tibial scaffold 80 with a set of load-sharing runners 82 oriented in a "longitudinal" direction, as well as a set of smaller reinforcing runners 84, which are not load-sharing, oriented in a "transverse" direction. In femoral scaffold 90, the orientation of the runner sets is reversed; the load-sharing runners 92 are transverse, while the smaller runners 94 are longitudinal. This differential orientation will help ensure that the two articulating scaffolds 80 and 90 will not catch or hang up on each other, and will not try to interlock when one scaffold's set of parallel ridges tries to settle into a complementary and parallel set of grooves in the other scaffold.

If desired, various patterns of non-linear runners (including honeycombed pattern, "parallel wavy" patterns, etc.) can be evaluated for strength and suitability. Depending on the thickness of the runners, the non-straight segments of cartilage that will fill the runner-protected compartments in this type of scaffolding pattern may be able to interlock with each other to an extent, and may help support and reinforce newly generated cartilage against various types of mechanical force and stress.

It also should be recognized that the desired level of support which needs to be provided by the runners in a scaffold is likely to vary between different patients. For example, in a frail elderly woman suffering from arthritis, a set of lesser or secondary runners might not need to provide any load-bearing support at all, and would not need to extend the entire height of the scaffold; this would allow a higher degree of intercommunication between the runner-protected compartments, which would essentially become relatively long and parallel compartments. However, in a large and heavy male, a set of lesser/secondary runners can be designed to offer additional support along with a set of main/primary runners, in a manner comparable to the runners 12 shown in FIG. 1. Alternately, if a honeycombed or other pattern is used, the distinction between main and lesser runners can be eliminated completely, and all runner segments can contribute equally to the load-sharing support offered by the scaffold.

The runners do not need to provide watertight barriers that will completely separate the scaffold compartments from each other. As suggested by FIG. 1, various types and sizes of vents, orifices, or other openings passing through the runners (and the outer rim, if desired) can be provided. If the chondrocyte cells in two adjacent compartments can be encouraged to effectively grow together, via a vent or orifice through a runner that separates them, a "connecting bridge" of cartilage can be generated inside the passageway through the runner. This type of bridge is likely to help stabilize and increase the strength of the complete cartilage structure that is generated by the chondrocyte cells inside the scaffold compartments.

It should be noted that any runner-protected compartment will have at least one open facet which is directly exposed to a bone surface. The bone surface provides a living foundation which is porous to nutrients and wastes, to which the implant can attach and heal, and form a stable living fixation. When properly supported by that foundation, and with additional structural aid and load-sharing protection from the scaffolding runners and compartments, the chondrocyte cells in the scaffold compartments will grow, reproduce, and secrete cartilage until each compartment has been properly filled with cartilage. If the scaffolding runners are made of a resorbing material, the runners themselves will gradually disappear, and the cartilage segments in the various compartments will gradually grow together, to form a complete and cohesive cartilage layer.

Load-bearing Materials and Palisades

Figure 4:
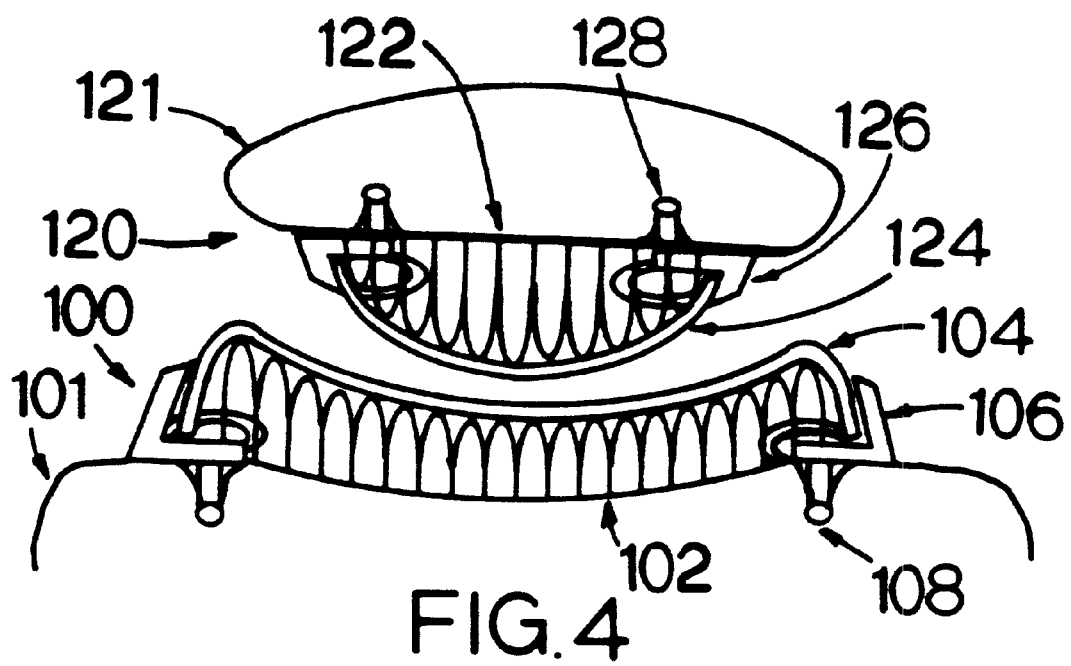
FIG. 4 is a cross-sectional view of palisade-type matrices comprising closely packed hollow tubes, supporting the articulating membranes in femoral and patellar scaffolds.
Figure 5:
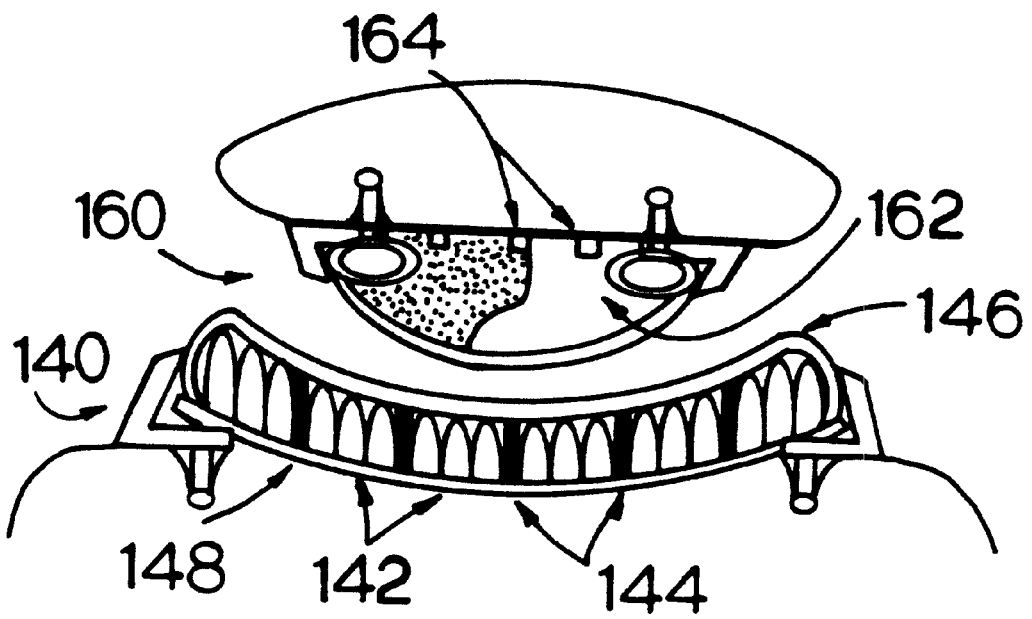
FIG. 5 depicts palisade-type matrices, as shown in FIG. 4, interspersed with runners that help support the weight-bearing loads imposed on the load-sharing scaffolds.

In an alternate preferred embodiment, illustrated in FIGS. 4 and 5, a load-sharing scaffold that can assist transplanted chondrocyte cells generate cartilage can be provided, not by a plurality of discrete runners, but by a much denser spacing of a generally porous but cohesive material. Such material can take any of a variety of forms, including: (i) a three-dimensional fibrous matrix which (unlike the highly porous collagen matrices disclosed in the prior art) is strong enough to actively share in supporting the weight-bearing loads that will be imposed on the scaffold; (ii) a matrix or other load-bearing structure (having, for example, numerous evenly spaced tiny pillars) made of a synthetic biodegradable polymer; and, (iii) a "palisaded" structure comprising numerous hollow tubules, packed together and oriented in the same direction to withstand a compressive load.

In general, collagen fibers are not well-suited for resisting compression. Like a strong rope or piece of string, they are good at withstanding and resisting tension, but they simply bend and fold if subjected to longitudinal compression. For this reason, collagen matrices with a desired level of porosity tend to be relatively weak, squishy, and sponge-like, especially under wet conditions. This lack of structural strength is also due to the fact that the porosity levels in collagen matrices designed to promote cell ingrowth are usually very high; typically, more than 90% of the volume of a cell-growing collagen matrix is pore space, where the cells will grow. Therefore, the collagen matrices disclosed in the prior art do not offer good candidates for use as load-bearing components, in load-sharing scaffolds as disclosed herein.

A preferred class of candidate compounds for use in a load-sharing scaffold includes synthetic polymers that are biodegradable. These can be synthesized and manufactured in highly controllable forms that can have substantial compressive strength, but which are gradually degraded by enzymes that naturally occur in human joints. Various types of biodegradable synthetic polymers that offer good candidates for such evaluation and development are discussed in U.S. Pat. No. 5,041,138 (Vacanti et al 1991). These can be synthesized and molded in any desired form, such as using numerous relatively thin "pillars" that are distributed across a surface area in a way that can support an articulating membrane.

Another type of structure that offers good promise for use in load-sharing scaffolds includes "palisaded" structures. This term refers to a structure comprising relatively narrow, closely-packed vertical components, such as a fence made of tall wooden stakes rather than wide flat boards. As is well known, hollow tubes tend to have a relatively high strength-to-weight ratios in resisting longitudinal compressive forces. Accordingly, a collection of hollow tubes that are packed closely together can provide excellent strength, to resist compression in the direction of the axis of the tubes. In addition, it should be noted that the type of cartilage (called hyaline cartilage) which covers the ends of bones, in joints, has a naturally palisaded internal structure.

Accordingly, palisaded matrices comprising closely-packed hollow tubes with relatively small diameters (such as about 3 to about 50 cell widths) offer good candidates in the field of biocompatible materials that can: (i) provide good physical support for a load-sharing scaffold; (ii) encourage chondrocyte cells to grow and reproduce inside the scaffold; and (iii) gradually degrade and disappear, leaving behind regenerated cartilage.

Palisade-type supporting structures are depicted (with the palisaded matrix enlarged, for clarity of illustration) in FIG. 4. This cutaway view is a cross-sectional view of a femoral scaffold assembly 100 and a patellar scaffold assembly 120. The femoral scaffold 100, shown in the lower half of the figure, comprises a palisaded matrix 102, which supports an articulating membrane 104. The matrix and membrane are both anchored to femoral bone 101 with the aid of a positioning ring 106 and anchors 108. In the upper half of FIG. 4, patellar scaffold 120 comprises palisaded matrix 122 and articulating membrane 124, anchored to patella 121 with the aid of a positioning ring 126 and anchors 128.

FIG. 5 illustrates a similar femoral scaffold assembly 140, in which palisade matrix 142 is interspersed with a plurality of load-bearing runners 144, to help support the articulating membrane 146. As depicted in FIG. 2, the patellar scaffold 160 also has load-sharing runners 162, oriented perpendicular to the femoral runners 144. Both scaffolds also have smaller reinforcing runners, shown as femoral runner 148 and patellar runner 164.

Selectively-permeable Outer Membranes

In one preferred embodiment, a resorbable scaffold as disclosed herein can be provided with a semi-permeable membrane on its outer (articulating) surface, to interact with certain molecular components of synovial fluid (i.e., the fluid which naturally fills and lubricates the contact surfaces between two cartilage segments in a joint). These membrane-fluid interactions in a joint with an implanted scaffold are intended to mimic the natural cartilage-fluid interactions in a healthy and unmodified joint.

To fully understand the types of membranes preferred for use with the scaffolds disclosed herein, one needs to have a working knowledge of certain physiological and fluid-flow aspects of healthy and unmodified cartilage surfaces in a joint such as a knee. The overview provided below (which is necessarily brief and highly simplified) is an analysis by the inventor/applicant herein, based upon numerous published articles. Those articles can be grouped into three major categories.

In the first category, articles which focus mainly upon non-fluid structural components of cartilage (either in naturally-occurring healthy form, or in diseased form) include Teshima et al, *J Bone Joint Surg Br* 77: 460 (1995), and Guilak et al, *J Orthoped Res* 12: 474 (1994).

In the second category, articles that focus mainly on the liquids which help lubricate a joint, or on the interactions between liquids and various fibers, membranes, etc., include Setton et al, *J Biomech* 26: 581 (1993), Oloyede et al, *Connect Tissue Res* 29: 251 (1993), Bernich et al, *Biochim Biophys Acta* 448: 551 (1976), Torzilla, *Med Biol Eng Comp* 31 *Suppl:* S93 (1993), Oloyede et al, *Connect Tissue Res* 30: 127 (1993), Murakami et al, *Proc Inst Mech Engr* [H] 212: 23 (1998), Hou et al, *J Biomech* 25: 247 (1992), Hlavacek, *J Biomech* 28: 1199 (1995), Higaki et al, *Proc Inst Mech Engr* [H] 212: 337 (1998), Williams et al, *Proc Inst Mech Engr* [H] 207: 59 (1993), Schwarz et al, *Br J Rheumatol* 37: 21 (1998).

In the third category, articles which focus on artificial devices that have been developed in the past (including artificial joints, candidate materials for use in joint repair, and cellular transplants) include Fisher et al, *Proc Inst Mech Engr* [H] 205: 73 (1993), Unsworth, *Proc Inst Mech Engr* [H] 205: 73 (1991), Williams et al, *Biomaterials* 16: 1169 (1995), Auger et al, *Proc Inst Mech Engr* [H] 207: 25 (1993), McClure et al, *Proc Inst Mech Engr* [H] 210: 89 (1996), Stewart et al, *Proc Inst Mech Engr* [H] 211: 451 (1997), Williams et al, *Proc Inst Mech Engr* [H] 211: 359 (1997), Gu et al, *Biomed Mater Engr* 8: 75 (1998), Ambrosio et al, *Proc Inst Mech Engr* [H] 212: 93 (1998), Corkhill et al, *J Biomater Sci Polym Ed* 4: 615 (1993), Oxley et al, *Biomaterials* 14: 1064 (1993), Badiger et al, *Biomaterials* 14: 1059 (1993), Szleifer, *Biophys J* 72: 595 (1997), Baker et al, *Cell Transplant* 6: 585 (1997), and Dror et al, *Biomater Devices Artif Organs* 7: 31 (1979).

The abstracts of all of these articles (and, indeed the complete texts of many of the articles they are abstracted from) can be obtained for free through the Internet, using one of the National Library of Medicine's search engines, such as at http://www.ncbi.nih.gov or http://www.igm.nih.gov.

Several acronyms and abbreviations that are commonly used in these and similar articles are worth noting, as follows: SF, synovial fluid; HA, hyaluronic acid, and its ionized or salt form, hyaluronate; DPPC, dipalmitoyl phosphatidyl-choline; SAPL, surface-active phospholipid; IPN, inter-penetrating network.

Briefly, the major components of synovial fluid (SF) inside a joint (such as a knee joint, which is used for purposes of illustration) include the following:

(1) water, which should be regarded as both a lubricant and as a solvent fluid, and which contains and carries various "macromolecules" that make the lubricant more slippery and viscous than plain water.

(2) hyaluronate (HA) molecules. These are naturally occurring polymers, with molecular weights ranging from about 50,000 up to about 8 million daltons. A molecule of hyaluronate normally is formed by stringing together a large number of alternating rings of glucosamine and glucuronate.

(3) monomeric and short-chain forms of glucosamine, glucuronate, chondroitin, and other relatively small molecules that form the building blocks of cartilage, hyaluronate, and other naturally-occurring compounds; and, (4) two compounds called "lubricin" and "surface-active phospholipid" (SAPL). These two types of molecules exist in both free form, and in a "complex" form that is held together by inter-molecular attraction rather than covalent bonding. In a lubricin/SAPL complex, a single molecule of lubricin is assumed to bind to a single molecule of SAPL. A lubricin/SAPL complex can be sheared apart or otherwise pulled apart by fluid flow or mechanical stress, without damaging either type of molecule. After this type of separation, it is assumed that the free molecules of lubricin and SAPL can recombine again, in solution.

Those are the primary known lubricating components of synovial fluid which are essential to understanding the statements and proposals in this application. They're shown in simplified schematic form in FIGS. 6A through 6E.

Figure 6A:
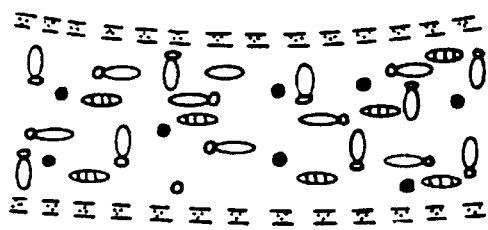
FIG. 6 (which includes parts 6A through 6E) depicts several natural physiological processes that are emulated by a selectively-permeable membrane which can be mounted on the outer (articulating) surface of a scaffold implant as disclosed herein.

FIG. 6A, labelled "Unloaded Joint Space", is a cross-sectional depiction of a small portion of a knee joint that is relaxed and not under pressure. The top and bottom "selectively permeable membranes" shown throughout FIGS. 6A through 6E represent only the outermost membranes that cover the opposing ("articulating") surfaces of two different segments of cartilage, on two different bones. In each part of FIG. 6, the upper membrane covers the bottom surface of a femoral runner, while the lower membrane covers the upper surface of a tibial plateau.

As indicated in FIGS. 6A–E, these two membranes (which cover two different opposing segments of cartilage) do not contact each other at all; instead, there is a gap between them. That gap is filled with synovial fluid, which contains water (the solvent) and the slippery components of a biological "soup", which includes hyaluronate molecules, lubricin/SAPL complexes, and various other molecules such as glucosamine, chondroitin, etc.

The outermost membranes which cover the femoral and tibial cartilage segments are "selectively permeable". In general, each cartilage membrane is composed of a thin layer, made up mainly of interconnected collagen fibers. Collagen is a fibrous protein, which forms the matrix that holds cells together in nearly all types of cohesive flexible tissue, including muscle tissue, skin, organs, etc. Each thin membrane made of interconnected collagen fibers allows water molecules to flow through it in a rate-controlled manner; as discussed below, this allows fluid loads and pressures to be redistributed across the membrane in a regulated manner as the joint is "loaded" with weight.

Each collagen membrane also allows some but not all of the "macromolecules" which lubricate the joint to permeate through that membrane. The massive hyaluronate molecules are assumed to not penetrate or permeate through the membranes at all, while the smaller building blocks of cartilage (such as glucosamine and chondroitin) can gradually permeate through the membranes, allowing them to reach the cartilage beneath the membranes. The exact relationship between the membrane and the different components of the lubricin/SAPL complexes is not yet fully understood; however, for purposes of the following simplified description, it is assumed that the lubricin molecules can either penetrate the collagenous membrane, or at least partially enter that membrane, while the SAPL molecules do not penetrate or enter the membrane at all (at least, not in substantial quantities).

Figure 6B:
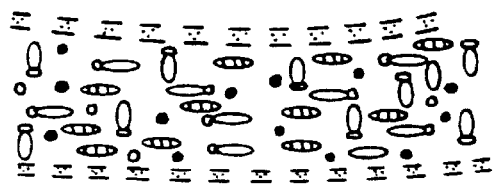

FIG. 6B (labelled "Instantaneous Loading") illustrates what happens when the joint is initially compressed after being at rest, such as when the person stands up. As the person goes through the motion of standing, the bottom surface of the femoral runner begins to slide toward the rear, on the the tibial plateau. As this type of sliding motion occurs, pressure is imposed on the joint, due to the weight of the person.

During this initial sliding and loading motion, within the zone of highest pressure within the joint, the cartilage surfaces on the femur and tibia initially engage in a "hydroplaning" motion. As this is occurring, the macromolecules in the synovial fluid are being compressed, as shown by their slightly greater density in FIG. 6B compared to the fluid in the relaxed joint of FIG. 6A. However, these macromolecules have not yet had time to begin permeating into either of the cartilage membranes, and the much smaller water molecules have had only an instant to commence that process. The two cartilage membranes do not contact each other during this "hydroplaning" stage; instead, the femoral runner is kept suspended above the tibial plateau by the layer of watery synovial fluid between them.

Figure 6C:
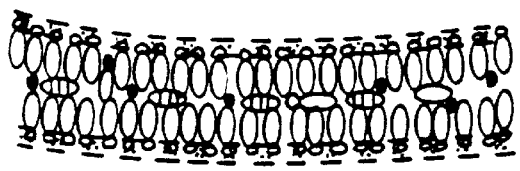

FIG. 6C ("Static Compression") schematically illustrates the condition that will arise within the zone of maximum compression inside the joint, if the person remains standing still for several minutes. Under sustained static pressure, the lubricin/SAPL complexes, which are forced to seek an arrangement that minimizes their volume, begin to line up in an aligned configuration as shown. The lubricin "heads" will, to at least some extent, contribute to this alignment between the cartilage membranes; although this process is not fully understood, it is assumed herein, for purposes of discussion and illustration, that the lubricin heads will fit into the interstitial spaces between adjacent collagen fibers in the cartilage membranes, and the SAPL "tails" project will away from the membrane, into the synovial fluid. In addition, this type of static compression will also tend to drive water molecules (which are much smaller and more mobile) out of the high-pressure zone with maximal compression, thereby increase the concentration of the remaining lubricant components in that zone, which will increase the thickness and viscosity of the lubricant fluid that remains.

Figure 6D:
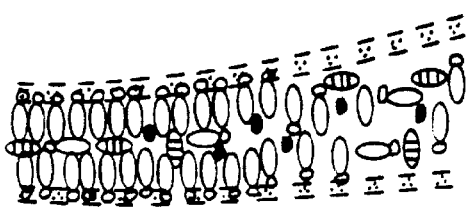

FIG. 6D ("Hydroplaning Motion") illustrates what happens if the person then begins walking forward, after standing still for a sustained period. Shear forces exerted on the synovial fluid by the relative motion of the two membranes cause the SAPL/lubricin concentrate in the contact zone to lubricate the initial launch of the joint into a hydroplaning mode of load transfer. As mentioned above, this type of action may cause at least some of the lubricin/SAPL complexes to be pulled apart or otherwise altered.

These various actions (including possible dissociation of SAPL from lubricin, mixing of the SAPL molecules with hyaluronate, and removal of water and other small solute molecules from the high-pressure zone) lead to formation of a highly viscous, slippery, "slimy" fluid between the two cartilage segments, when the person is standing still. Upon initiation of walking, the surfaces begin a "hydroplaning" interaction relative to each other, and thereby promote the clearing of the surface membranes for future alignment of lubricin/SAPL complexes when the joint is subsequently statically loaded.

Because of its viscous and slimy nature (and, it is hypothesized herein, because free SAPL molecules in the viscous fluid may be attracted to lubricin molecules that have become embedded in the surfaces of the cartilage membranes), the lubricating components of the synovial fluid (mainly hyaluronate and SAPL molecules) continue to keep the two cartilage segments separated from each other, so that the two opposing cartilage segments still do not directly contact each other, even if the person continues to walk or run. This is part of a natural mechanism of fluid cushioning and fluid insulation, which allows cartilage segments in knee and hip joints to remain intact, undamaged, and unabraded, despite all the wear and motion that is imposed on those joints for 70 or 80 years or more, in a healthy person.

Figure 6E:
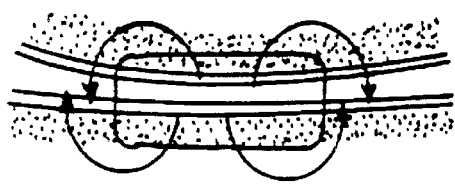

FIG. 6E depicts another apparently important factor in a "tribological" analysis of how synovial fluids can manage to lubricate knee and hip joints so successfully (for the most part) for decades. There are 4 semi-circular arrows shown in FIG. 6E. These arrows schematically depict pressures and directional fluid flows, across the two membranes that cover the cartilage segments. These arrows indicate that, in the regions which surround and flank the center of a high-pressure loading zone, water molecules inside the cartilage "gel" (beneath the covering membranes) in each segment of cartilage are being forced out and away from the central zone where the pressure is highest. These water molecules can flow through the gel, but only slowly, because the fibrous molecular matrix that holds the gel together constrains molecular flow through the gel.

As water molecules in the area of highest pressure inside a knee joint do their best to shift and flow outwardly into the flanking areas, they exert pressure against the surrounding water molecules, which fill the cartilage gel that surrounds the highest pressure region. As indicated by the arrows in FIG. 6E, this type of pressure, acting on small and mobile water molecules that are trapped inside a segment of cartilage gel, causes the semi-permeable membranes which cover the two cartilage segments to be pushed toward each other, from beneath, rather than away from each other, in the areas that flank and surround the center zone of highest pressure.

This type of fluid response, by small and semi-mobile water molecules trapped inside a gel structure, causes two important results. The first involves a more even distribution of pressure within a weight-bearing joint, such as a knee joint in a person standing upright. Since the pressures and constrained motions of water inside a cartilage gel cause the surrounding areas of cartilage to press outwardly, away from their bones, those surrounding regions will help support and bear a larger portion of the weight that is being imposed on that knee joint. This type of cooperative assistance, by a roughly ring-shaped circle of cartilage surrounding the center zone of maximum pressure, helps ensure that no single small area of cartilage is forced to bear the entire weight of a person's body. Obviously, this type of pressure-sharing response is important in helping prevent potentially abrasive and destructive direct contact between two opposing segments of cartilage in a knee or hip joint.

The second effect may be equally important, on a long-term basis. The flow of small and mobile water molecules, within the cartilage gel, helps free embedded macromolecules (including lubricin molecules) from the semi-permeable collagenous membrane which covers a cartilage segment. In other words, the motion of water molecules within and through cartilage gel may help "blow out" and rinse out the selectively permeable collagen membrane that covers that segment of cartilage; this can dislodge and remove any lubricin, SAPL, hyaluronate, or other macromolecules that have become embedded in the semi-permeable collagen membrane, and may help clear the membrane for subsequent interactions with fresh lubricin/SAPL complexes. This type of constrained flow of small water molecules through a gel matrix may also help generate and ensure substantially higher levels of travel and permeation of the nutrient building blocks (including glucosamine and chondroitin) through both the semi-permeable membrane which covers a segment of cartilage gel, and through the cartilage gel itself.

With that as background information, a synthetic membrane for use on the articulating surface of a resorbable scaffold as disclosed herein can be composed of suitable fibers, made of collagen or a suitable resorbable, hydrophilic, synthetic polymer. Preferably, the membrane should be woven or otherwise fabricated such that the fibers are oriented parallel to the articular surface (i.e., in the "tangential" orientation).

The undersurface of the membrane can also be provided with interwoven fibers that extend downward, generally perpendicular to the membrane surface (referred to as the "radial" direction, since most cartilage surfaces are generally round). These radially extending fibers will facilitate the interdigitation of these fibers into the residual cartilage radial layer. If desired, such semi-rigid radial fibers on the undersurface of a membrane can be provided with hooks/barbs on the ends, to promote a "velcroid" type of adherence of the membrane to the collagen (and, to a lesser extent, glycosaminoglycan) fibers which hold together the cartilage hydrogel, at the depths of the residual chondral radial layer. Alternately or additionally, various adhesive compounds (such as fibrin glue) and mechanical devices (such as suture tacs or anchors) can also be used to help secure a membrane to a cartilage surface or implant. If desired, mesenchymal stem cells (which can be obtained most easily from bone marrow aspirates) can be used to populate a membrane undersurface, prior to or during surgical implantation.

Figure 7:
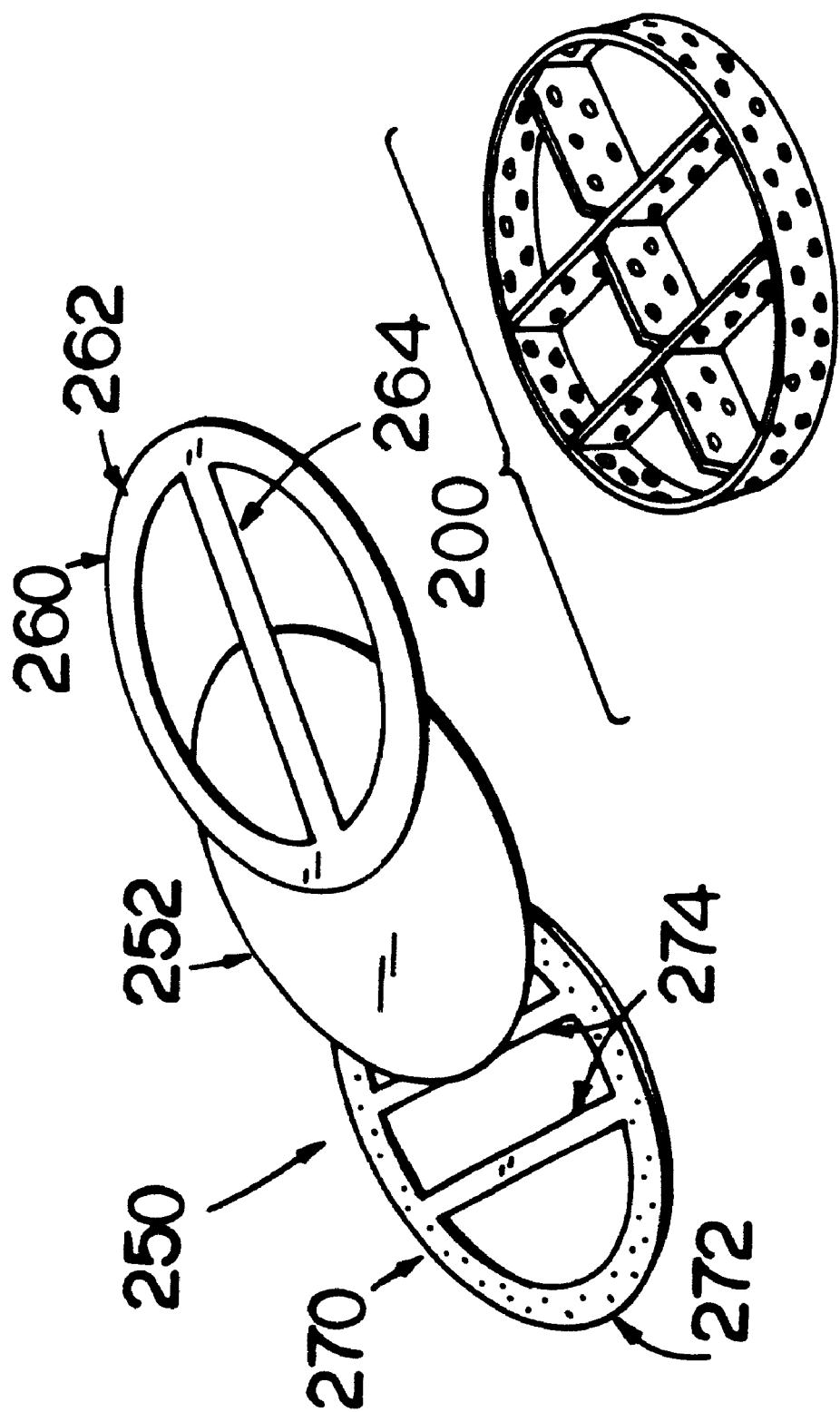
FIG. 7 depicts the assembly of a resorbable scaffold with a selectively-permeable outer membrane having certain desired and useful traits.

In one preferred embodiment, the fabrication of a scaffold assembly containing rim and runner components as disclosed herein, coupled to a thin surface membrane, can be carried out by first fabricated the rim and runner components into a subassembly, and then bonding the membrane to that "scaffold base" subassembly. This approach is illustrated in FIG. 7, which illustrates a scaffolding base 200 comprising an outer rim 210, two transverse runners 212 and 214, and a longitudinal runner 220. These runners in conjunction with the rim 210 subdivide the area covered by scaffolding base 200 into six substantially smaller areas, so that each smaller area can be filled with a cell slurry, or a highly porous scaffolding material that will promote rapid cell growth and cartilage generation.

Three layers which comprise membrane assembly 250 are shown in FIG. 7. The primary component of this membrane assembly 250 is a flat continuous membrane 252, which will cover the entire outermost surface of scaffolding base 200. In the configuration shown in FIG. 7 (which is one possible design out of numerous possible designs), bidirectional selectively-permeable membrane 252 will be "sandwiched" within, and supported and strengthened by, an upper layer 260 (with a rim 262 and a single longitudinal runner 264) and a lower layer 270 (with a rim 272 and two transverse runners 274). All three layers which form lid assembly 250 are intended to be relatively thin, such as less than 1 or 2 mm around the rim, at the thickest aggregate part. The lid subassembly 250 is created outside the joint, and may be created by any of several possible methods (such as a sandwiching assembly operation, molding of a single integrated component, etc.).

The rims of the upper layer 260 and lower layer 270 (and possibly the runners 264 and 274 of the lower and upper layers as well), and one or more interacting components of the base assembly 200, will interact to provide a means for mechanically "snapping" the membrane subassembly 250 onto the scaffolding base subassembly 200. In some approaches, this type of "snapping" final assembly operation can be performed outside a joint that is being repaired; in other approaches, it might be performed inside the joint, after the base assembly has been completely positioned and anchored inside the joint and then filled, via an insertion cannula, with a paste, slurry, or other preparation of transplanted cells, or with a plurality of rapid-growth scaffolding segments that have been or can be seeded with cells.

It should also be noted that it may be possible to use a snap-on lid assembly which places an "oversized" membrane over a scaffolding base assembly, such as assembly 200 in FIG. 7. In this type of approach, the center portion of the oversized membrane which covers and rests on top of the base assembly will be held in a relatively taut arrangement, by the outer rims of the final assembly, while an additional portion of the membrane periphery can overlap beyond the outer rim of the base assembly. This design can be regarded as an "apron" membrane assembly. Such an apron can be designed to cover a cartilage area which has lost its normal surface membrane; because of the abrading process that leads to most cartilage defects, it is very common for a cartilage defect to be surrounded by a substantially larger area of damaged external membrane, which can be covered by an apron, as suggested above. If desired, such an apron can be tacked down, at one or more locations around its periphery, using previously developed devices, to further stabilize the grid lid and scaffold.

It should be noted that somewhat similar efforts have been made by earlier researchers, using entirely different technology, using pieces of harvested periosteum (a naturally occurring thin collagenous membrane which normally surrounds bones). Although those prior efforts have shown some limited success, fixation over large areas has proven very difficult. The techniques disclosed herein may permit the arthroscopic insertion of surface membranes over larger surface areas than have previously been feasible using either arthroscopic or open-surgical techniques. Accordingly, such approaches may deserve to be reevaluated in light of the technology disclosed herein.

Regardless of which specific approach is used, the important aspect of this design is that once this type of device has been implanted inside a joint, and is loaded with transplanted chondrocyte cells that are ready to begin making new cartilage, the outermost articulating membrane of the scaffolding assembly can begin to function as a "selectively-permeable" bi-directional outer membrane layer, designed to emulate the selectively permeable bi-directional outer membrane of natural cartilage. As such, the material that would be chosen to form this type of implanted membrane would be selected in order to provide the selective permeability and various advantages of a naturally occurring outer membrane, as briefly summarized herein and as discussed in more detail in various articles that analyze the components and fluids in a healthy joint.

In particular, a "selectively-permeable" membrane for use as disclosed herein should be permeable to water, normal nutrients with low molecular weights, and to low-molecular-weight cellular waste products. However, such a membrane should be impermeable to surface-active phospholipids, hyaluronic acid, and the other macromolecular components of synovial fluid which, in a healthy joint, stay outside of the cartilage hydrogel, and remain dissolved or suspended in the synovial fluid between two cartilage surfaces.

Indeed, the study and realization, by the inventor and applicant herein, of the crucial roles that a selectively-permeable bi-directional membrane plays in cartilage has also led to an enhanced appreciation of the role that a surrounding selectively permeable bi-directional membrane is likely to play in other types of surgery which uses resorbable scaffolds, seeded with selected types of cells, to regenerate internal organs (such as a liver, spleen, pancreas, etc.) or other organized tissues. Accordingly, the technology discussed herein can also be adapted for use in tissue regeneration efforts using such resorbable scaffolds, to repair, regenerate, or replace such internal organs and other tissue. Such a surface membrane can be provided on one or more surface areas of the resorbable scaffold, and in the case of an internal organ, can provide a capsule which encloses essentially the entire resorbable scaffold. Once in place, the membrane can facilitate the absorption and retention of nutrients and functional molecules in one direction, and the release of waste and various functional molecules (such as hormones, metabolites, etc.) in the other direction, by the regenerating tissue, while at the same time using its selective permeability to help sustain the desired homeostatic balances and concentrations of various types of macromolecules in fluids on both sides of the membrane.

In addition, any such membrane can be seeded with one or more selected types of stem cells, either prior to the surgery or during the surgical implantation procedure, on the interior side of the membrane (i.e., the surface which contacts the resorbable scaffold). Such stem cells, if properly selected for a particular use, can help accelerate and promote rapid and effective healing, and can help minimize the formation of scar tissue.

Thus, there has been shown and described a new and useful type of load-sharing resorbable scaffold which can help transplanted chondrocyte cells repair cartilage defects in mammalian joints. Although this invention has been exemplified for purposes of illustration and description by reference to certain specific embodiments, it will be apparent to those skilled in the art that various modifications, alterations, and equivalents of the illustrated examples are possible. Any such changes which derive directly from the teachings herein, and which do not depart from the spirit and scope of the invention, are deemed to be covered by this invention.

REFERENCES

Brittberg, M., et al, "Treatment of deep cartilage defects in the knee with autologous chondrocyte transplantation," *New England J Medicine* 331: 889–895 (1994)

Chen, F. S., et al, "Chondrocyte transplantation and experimental treatment options for articular cartilage defects," *Amer J Orthopedics* 26: 396–406 (1997)

Ma, P., et al, "Development of biomechanical properties and morphogenesis of in vitro tissue engineered cartilage," *J Biomed Mater Res* 29: 1587–1595 (1995)

Ma, P., et al, "Morphology and mechanical function of long-term in vitro engineered cartilage," *J Biomed Mater Res* 44: 217–221 (1999)

Minas, T., et al, "Current concepts in the treatment of articular cartilage defects," *Orthopedics* 20: 525–538 (1997)

Rosengard, B. R., et al, "Selective breeding of miniature swine leads to an increased rate of acceptance of MHC-identical, but not of class I-disparate, renal allografts," *J. Immunol.* 149: 1099–103 (1992)

Thornhill, T. S., "Cartilage resurfacing: Facts, fictions, and facets," *Orthopedics* 20: 819–820 (1997)

Vunjak-Novakovic, G., et al, "Bioreactor cultivation conditions modulate the composition and mechanical properties of tissue engineered cartilage," *J Orthoped Res* 17: 130–138 (1999)

What is claimed is:

1. A surgically implantable device for repairing a segment of damaged cartilage in a mammalian joint, comprising a biocompatible scaffold which is designed and fabricated to promote formation of cartilage by chondrocyte cells which can be embedded therein prior to surgical implantation, and wherein the biocompatible scaffold has an articulating surface on a first side and an anchoring surface on an opposed second side, and wherein the biocompatible scaffold comprises:

a. at least one first portion made of a first relatively stiff matrix material which is porous, is gradually resorbable when in contact with body fluids, and promotes cell replication and secretion of cartilage-forming constituents by transplanted cells embedded within said first portion, and which is designed to withstand and resist a compressive articulating load placed on the joint after surgical implantation of the biocompatible scaffold but before substantial resorption of the first matrix material;

b. at least one second portion made of a second matrix material which is porous and gradually resorbable and which is designed and fabricated to promote optimal rapid cartilage formation following surgical implantation, by chondrocyte cells or mesenchymal stem cells embedded within the second matrix material or by progeny cells thereof.

2. The surgically implantable device of claim 1, wherein the first relatively stiff matrix material is shaped as a wall structure which defines and encloses at least one internal cell-growth compartment which is open to fluid flow on the articulating and anchoring sides of the surgically implantable device, and wherein the internal compartment contains a segment of the second matrix material.

3. The surgically implantable device of claim 1, wherein the first relatively stiff matrix material is shaped as an outer peripheral wall which encloses at least one internal runner which is coupled at both ends to the outer peripheral wall, wherein the outer peripheral wall and runner(s) establish and define a plurality of internal cell-growth compartments which contain segments of the second matrix material.

4. The surgically implantable device of claim 3, wherein each internal cell-growth compartment has a surface area of about 1 square centimeter or less in the open anchoring surface.

5. The surgically implantable device of claim 1, wherein the first relatively stiff matrix material has a dynamic stiffness in the range of about 3 to about 30 megapascals.

6. The surgically implantable device of claim 1, wherein the first relatively stiff matrix material has an aggregate modulus in range of about 200 to about 900 kilopascals.

7. The surgically implantable device of claim 1, wherein the articulating surface is covered by a porous membrane.

8. The surgically implantable device of claim 7, wherein the porous membrane is permeable to water and low molecular weight nutrients, and is not permeable to surface-active phospholipids.

9. The surgically implantable device of claim 7, wherein the porous membrane is seeded with mesenchymal stem cells on at least one surface which contacts the resorbable scaffold, prior to surgical implantation.

10. The surgically implantable device of claim 1, wherein the biocompatible scaffold is sufficiently flexible in hydrated form to allow the device to be inserted into a joint arthroscopically.

11. A surgically implantable device designed for repairing damaged cartilage in an articulating joint, comprising a resorbable scaffold having an articulating surface, an opposed anchoring surface, and at least two wall components which extend from the articulating surface to the opposed anchoring surface, wherein:

(a) the device is designed for surgical implantation into a cartilage defect surface area, in a manner which anchors and secures the anchoring surface of the device against an existing bone or cartilage surface, leaving the articulating surface of the device exposed;

(b) the wall components of the device, after surgical implantation, will subdivide the cartilage defect surface area into smaller areas; and, (c) the wall components of the device, after surgical implantation, will create a plurality of protected enclosed compartments, each of which will promote chondrocyte cell maturation and development of hyaline cartilage within that protected enclosed compartment.

12. The surgically implantable device of claim 11, wherein the articulating surface is covered by a porous membrane.

13. The surgically implantable device of claim 11, wherein the porous membrane is permeable to water and low molecular weight nutrients, and is not permeable to surface-active phospholipids.

14. The surgically implantable device of claim 11, wherein the articulating surface is covered by a porous membrane.

15. The surgically implantable device of claim 14, wherein the porous membrane is permeable to water and low molecular weight nutrients, and is not permeable to surface-active phospholipids.

16. The surgically implantable device of claim 14, wherein the porous membrane is seeded with mesenchymal stem cells on at least one surface which contacts the resorbable scaffold, prior to surgical implantation.

17. A method of repairing a cartilage defect in an articulating joint, comprising surgical implantation of a device of claim 11 into a cartilage defect surface area in the joint.

18. A method of repairing a cartilage defect in an articulating joint, comprising surgical implantation of a device of claim 15 into a cartilage defect surface area in the joint.

19. The method of claim 17, wherein the device is seeded with chondrocyte cells or stem cells which can form chondrocyte cells prior to surgical implantation.

20. The method of claim 17, wherein the device is seeded with chondrocyte cells or stem cells which can form chondrocyte cells during a surgical implantation procedure.

21. A surgical implant device for repairing a segment of damaged cartilage in a mammalian joint, comprising a resorbable cell-growing scaffold which is designed and fabricated to promote formation of cartilage by transplanted cells embedded within the scaffold, wherein the scaffold comprises a continuous peripheral wall which establishes and encloses at least one internal compartment suited for growing cells following surgical implantation, wherein the peripheral wall further establishes an articulating surface on a first side of the scaffold and an anchoring surface which is open to fluid flow on an opposed second side of the scaffold, and wherein the peripheral wall is made of a porous matrix material which is gradually resorbable when in contact with body fluids, and which prior to biological resorption following surgery has sufficient strength and stiffness to withstand and resist a compressive articulating load placed on the joint after surgical implantation of the scaffold, in a manner which allows a moderate compressive load to be placed on any fluid and cells in each internal compartment enclosed within the peripheral wall, in a manner which promotes formation of hyaline cartilage within each internal compartment following surgery and also allows formation of hyaline cartilage by cells embedded within the porous matrix material of the peripheral wall, following surgical implantation.

22. The cell-growing scaffold of claim 21, wherein the peripheral wall further encloses at least one internal runner which is made of the same matrix material and which subdivides the internal compartment enclosed within the peripheral wall into a plurality of internal subcompartments enclosed within the peripheral wall.

23. A surgical implant device for repairing a segment of damaged cartilage in a mammalian joint, comprising a resorbable scaffold which is designed and fabricated to promote formation of cartilage by transplanted cells protected by the scaffold following surgical implantation, wherein the scaffold comprises a continuous outer peripheral wall and at least one internal runner, wherein:

(a) the outer peripheral wall and runner(s), working together, establish and define a plurality of internal compartments which will be suited for holding cartilage-forming cells following surgery;

(b) the outer peripheral wall and runner(s) further establish an articulating surface on a first side of the scaffold, and an anchoring surface which is open to fluid flow on an opposed second side of the scaffold;

(c) the outer peripheral wall and runner(s) are made of a material which is gradually resorbable when in contact with body fluids, and which prior to biological resorption following surgery has sufficient strength and stiffness to withstand and resist a compressive articulating load placed on the joint after surgical implantation of the resorbable scaffold into the joint, in a manner which allows a moderate compressive load to be placed on any fluid and cells within each internal compartment, thereby promoting formation of hyaline cartilage within each internal compartment following surgical implantation.

24. A surgical implant device of claim 23, wherein the outer peripheral wall and runner(s) of the resorbable scaffold are made of porous material which can contain cells.

* * * * *